United States Patent [19]

Nagaoka et al.

[11] Patent Number: 5,135,800
[45] Date of Patent: Aug. 4, 1992

[54] OBLIQUELY ORIENTED POLYPROPYLENE CROSS FILM AND FASTENING TAPE FOR PAPER DIAPER COMPRISING SAID CROSS FILM

[75] Inventors: Haruki Nagaoka; Shuzo Sasagawa; Kazunari Nishino, all of Waki, Japan

[73] Assignee: Mitsui Petrochemical Industries, Ltd., Tokyo, Japan

[21] Appl. No.: 324,163

[22] Filed: Mar. 13, 1989

[30] Foreign Application Priority Data

Mar. 14, 1988 [JP] Japan ................................... 63-58419
Jun. 2, 1988 [JP] Japan ............................. 63-72747[U]

[51] Int. Cl.⁵ ........................ B32B 27/32; B32B 7/06; C09J 7/02; A44B 21/00
[52] U.S. Cl. ..................................... 428/216; 428/218; 428/354; 428/355; 428/352; 428/910; 428/516; 428/41; 428/520; 428/476.9; 428/414; 428/424.8; 428/519; 604/389; 604/390; 427/208.8; 427/39; 427/208.2; 156/244.11; 156/500
[58] Field of Search ............... 428/516, 910, 216, 218, 428/354, 355, 352, 41, 520

[56] References Cited

FOREIGN PATENT DOCUMENTS

| | | | |
|---|---|---|---|
| 812758 | 5/1969 | Canada | 428/516 |
| 0216300 | 4/1987 | European Pat. Off. | 428/516 |
| 0321957 | 6/1989 | European Pat. Off. | 428/516 |
| 0034834 | 3/1978 | Japan | 428/516 |

*Primary Examiner*—P. C. Sluby

[57] ABSTRACT

A composition comprising polypropylene and a small amount of polyethylene can be shaped into an obliquely oriented film, and if obliquely oriented films shaped from this composition are laminated so that the molecular orientation directions cross one another, an obliquely oriented cross film having excellent heat resistance and mechanical strength is obtained. This cross film is suitably used as a base of a fastening tape for a paper diaper.

6 Claims, 1 Drawing Sheet

OBLIQUELY ORIENTED POLYPROPYLENE CROSS FILM AND FASTENING TAPE FOR PAPER DIAPER COMPRISING SAID CROSS FILM

BACKGROUND OF THE INVENTION (1) Field of the Invention

The present invention relates to an obliquely oriented polypropylene cross film. More particularly, the present invention relates to an obliquely oriented polypropylene cross film comprising a plurality of polypropylene films formed of a polypropylene/polyethylene composition comprising polypropylene as the main component and having a molecular orientation in a certain oblique direction, which are laminated so that the molecular orientation directions of the films cross one another, and a fastening tape for a paper diaper, having excellent mechanical strength, heat resistance and softness, in which the above-mentioned cross film is used at least as a part of a base of the tape.

(2) Description of the Related Art

It is known that an obliquely oriented cross film formed by laminating two polyethylene films having a molecular orientation in a certain oblique direction so that the molecular orientation direction cross each other is used for various packaging materials. For example, Japanese Utility Model Publication No. 19087/81 and Japanese Utility Model Publication No. 20590/86 teach that a cross film as mentioned above is used as a packaging bag for a photosensitive material, and Japanese Utility Model Publication No. 13637/85 teaches that a cross film as mentioned above is used as a self-supporting packaging bag.

High-density polyethylene is used as the starting material for these known obliquely orientated cross films. The reason is that since high-density polyethylene has a sufficient melt tension at the melt extrusion, the film-forming property is excellent. Since this obliquely oriented cross film composed of high-density polyethylene has a resistance against impact and rupture and a good balance of tensile strength and elongation, the cross film is used for various packaging materials. However, the cross film is defective in that the heat resistance is poor, and therefore, the use is limited to packaging materials as mentioned above.

It is well known that polypropylene is superior to polyethylene in the heat resistance, but polypropylene involves a serious technical problem. Namely, if it is intended to shape polypropylene into an obliquely oriented film, since the melt tension is insufficient at the extrusion of polypropylene from an extruder, it is impossible to obtain a self-supporting, obliquely oriented film.

An adhesive tape fastener used as the fastening member of a paper diaper comprises a fastening tape for fastening the front and back parts of the paper diaper to maintain a trunk-like shape, a release tape temporarily fixed to the paper diaper proper before the use and acting as the temporarily fixing base when released and used, and an intertape located between the fastening tape and the release tape before the use, which is bonded to the front part of the paper diaper during the use to act as the temporarily fixing member for the fastening tape and can release the fastening tape repeatedly.

As the base of the fastening tape, there have been used a nonwoven fabric, a paper, a polyethylene film, a polypropylene film and the like.

For the fastening tape, it is required that the tensile strength and tear strength of the base should be high for preventing breaking of the tape, the interface between the sticking agent and the base should be stabilized for preventing peeling of the sticking material, and the softness and heat resistance should be high.

However, the above-mentioned conventional bases are poor in the tensile strength or tear strength and are also defective in that the softness and heat resistance are poor. If the tensile strength or tear strength is poor, while binding and peeling are repeated between the fastening tape and the intertape during the use of the paper diaper, the fastening tape is broken. If the film is poor in the softness, an underwear of a baby or the hand of a handler is often damaged by the end or section of the film during the use of the diaper. Furthermore, if the heat resistance of the film is poor, the film is curled by heating at the step of coating the sticking agent on the molten surface of the film, and the operation of coating the sticking agent becomes difficult.

SUMMARY OF THE INVENTION

It is therefore a primary object of the present invention to provide an obliquely oriented polypropylene cross film having excellent heat resistance and mechanical strength, which is formed from a composition obtained by blending a small amount of polyethylene into polypropylene to make shaping of an obliquely oriented film possible, and is obtained by preparing obliquely oriented films from this composition and laminating these films so that the molecular orientation directions cross one another.

Another object of the present invention is to provide a fastening tape for a paper diaper, which has high tensile strength and tear strength and excellent softness and heat resistance.

Namely, the present invention is to provide an obliquely oriented cross film having excellent heat resistance and softness and a fastening tape in which this cross film is used at least as a part of a base of the tape, and the present invention is characterized in that a specific polypropylene composition is used.

More specifically, in accordance with one aspect of the present invention, there is provided an obliquely oriented polypropylene cross film, which comprises a plurality of polypropylene films having a molecular orientation in a certain oblique direction, which are laminated so that the molecular orientation directions cross one another, said polypropylene films being shaped from a composition comprising 50 to 90 parts by weight polypropylene and 10 to 50 parts by weight of polyethylene.

In accordance with another aspect of the present invention, there is provided a fastening tape for a paper diaper, which is characterized in that the above-mentioned obliquely oriented polypropylene cross film is used at least as a part of base of the tape.

Figure 1:
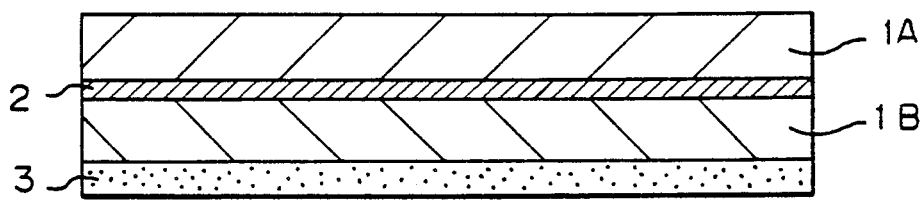
FIGS. 1 and 2 are sectional views showing examples of the fastening tape for a paper diaper according to the present invention.

In the drawings, each of reference numerals 1A and 1B represents an obliquely oriented propylene film, each of reference numerals 2 and 4 represents an adhesive layer, reference numeral 3 represents a sticking agent layer, and reference numeral 5 represents a synthetic resin film.

DETAILED DESCRIPTION OF THE PREFERRED EMBODIMENTS

The present invention is based on the finding that since a composition formed by blending 50 to 90 parts by weight of polypropylene with 10 to 50 parts by weight of polyethylene has a sufficient melt tension when a film is shaped by melt-extruding the composition from an extruder, the composition can be shaped into a self-supporting, obliquely oriented film. Since this obliquely oriented cross film has excellent heat resistance and softness, this obliquely oriented film can be used even in the field where high heat resistance and softness are required.

The cross film of the present invention is characterized in that the cross film is prepared by laminating a plurality of films formed from a composition obtained by blending 50 to 90 parts by weight of polypropylene with 10 to 50 parts by weight of polyethylene and having a molecular orientation in a certain oblique direction, so that the molecular orientation directions cross one another.

If the amount of polypropylene is smaller than 50 parts by weight, no sufficient heat resistance can be obtained, and if the amount of polypropylene is larger than 90 parts by weight, the melt tension is insufficient and therefore, at the step of preparing an obliquely oriented film, the molten film is caught on a mandrel or edge plate, and a puncture is caused and oblique orientation by drawing becomes impossible.

A homopolymer of propylene having a melt flow rate (MFR) or 0.5 to 10 g/10 min, especially 0.5 to 2.0 g/10 min, is preferably used as the polypropylene. However, a random or block copolymer of propylene as the main component with other olefin can be used as the polypropylene.

As the olefin to be copolymerized with propylene, there can be mentioned 1-olefins having up to 10 carbon atoms, such as 1-butene, 1-pentene, 3-methyl-1-pentene, 1-hexene, 4-methyl-1-pentene, 1-octene and 1-decene. A copolymer of propylene with ethylene is especially preferred.

This comonomer component is used in an amount of up to 15 mole%, preferably up to 10 mole%, in case of a random copolymer, and in case of a block polymer, the comonomer is used in an amount not degraded the heat resistance of the polypropylene, generally up to 50 mole%, preferably up to 40 mole%. If MFR of the polypropylene is within the above-mentioned range, excellent heat resistance and softness can be given to the film.

High-density polyethylene having a density of 0.940 to 0.965 g/cm$^3$, especially 0.940 to 0.960 g/cm$^3$, and MFR of 0.01 to 10 g/10 min, especially 0.030 to 2.0 g/10 min, is preferably used as the polyethylene. However, a copolymer of ethylene as the main component with other olefin can be used as the polyethylene.

As the olefin to be copolymerized with ethylene, there can be mentioned up to 50 mole% of propylene or a 1-olefin having up to 10 carbon atoms, such as 1-butene, 1-pentene, 3-methyl-1-butene, 1-hexene, 4-methyl-1-pentene, 1-octene or 1-decene.

If the amount, density and MFR of the polyethylene are within the above-mentioned ranges, excellent shapeability and mechanical strength can be given to the film.

Incidentally, if the above-mentioned copolymer composed mainly of propylene is used as the polypropylene, it is preferred that an ethylene/propylene copolymer composed mainly of ethylene be used as the polyethylene and both of the copolymers be blended so that the total content of the propylene content in the entire composition be at least 50% by weight.

A known method can be adopted for preparing an obliquely oriented film to be used as the starting film for the obliquely oriented cross film of the present invention. For example, there can be mentioned a method in which a tubular film obtained by the inflation method is drawn in the axial direction and is then spirally cut and opened (see Japanese Patent Publication No. 5319/65), a method in which a tubular film extruded by a circular die is spirally oriented by a mandrel and a pinch roll, which are continuously turned, while the film is elongated in the film-forming direction, and the oriented film is folded after or without cutting and opening the film in the film-forming direction (see Japanese Patent Publication No. 38621/72), a method in which a tubular film extruded by a circular die is arranged between a stationary mandrel and a rotating mandrel, the film is drawn and oriented in an oblique direction between the two mandrels, and the drawn film is taken up by a pinch roll and a pulling roll (see Japanese Patent Publication No. 38306/78), and a method in which an obliquely oriented film is prepared by using an apparatus in which a circular die and a first mandrel are rotated, a second mandrel of a pulling roller is rotated in the opposite direction so that distortion of a tubular film to the pulling roll is compensated, and shaping can be carried out without rotating the pulling roll and a winding roll (see Japanese Patent Publication No. 15892/79). A method using an apparatus proposed by us in Japanese Patent Publication No. 38306/78 or No. 15892/79 is especially preferred because an appropriate strength can be obtained by drawing and obliquely orienting the film at an optional orientation ratio.

The orientation ratio (the ratio of the strength of the drawn film to the tensile strength of the undrawn film) of the starting film is appropriately decided according to the intended use, but it is generally preferred that the orientation ratio of the starting drawn film be at least 1.2, especially about 1.5 to about 5. Furthermore, the direction of the orientation axis should be appropriately decided according to the intended use. In general, it is preferred that when the starting films are bonded so that the orientation direction cross one another, the crossing angle between the two orientation directions be 30° to 150°, especially 60° to 120°, in the length directions of the starting films.

Various methods can be adopted for bonding starting films as mentioned above. For example, there can be mentioned a dry lamination method in which one starting film is coated with a vinyl, polyamide, epoxy, rubber or urethane adhesive, the adhesive is dried and the remaining starting film is heat-bonded under pressure to the adhesive-coated starting film, an extrusion lamination method in which one starting film is subjected to a corona treatment and/or an anchoring treatment with an organic titanium, polyethylene-imine or isocyanate type anchoring agent, extrusion-laminating low-density polyethylene (by the high-pressure method or the low on medium-pressure method) or an ethylene/vinyl acetate copolymer on the treated starting film and the remaining starting film is press-laminated on the laminated starting film, and a hot-melt lamination method. A composition formed by blending low-density polyethylene having a density of 0.91 to 0.93 g/cm$^3$ and MFR of 5 to 20 g/10 min with 10 to 40% by weight, preferably 25 to 35% by weight, of an ethylene/α-olefin random copolymer is especially suitable as the adhesive resin for laminating the polypropylene films according to the present invention.

Incidentally, a laminated cross film is directly formed by using the obliquely oriented film-shaping apparatus in which an obliquely oriented film is obtained by relatively rotating a circular die and a pulling roll, as disclosed in Japanese Patent Publication No. 38621/72 or No. 38306/78. The bonding strength or lamination strength between the obliquely oriented films should ordinarily be at least 10 g/15 mm. In order to obtain an obliquely oriented drawn cross film having a tear strength well-balanced in the longitudinal and lateral directions, it is preferred that the bonding strength be maintained in the range of from 50 to 600 g/15 mm, especially 100 to 400 g/15 mm. Even if the bonding strength exceeds 400 g/15 mm, no particular problem arises, but the tear strength is somewhat reduced in the longitudinal direction in the obtained product.

The obliquely oriented cross film of the present invention has the above-mentioned structure. Known additives such as a heat stabilizer, an antioxidant, a bulking agent, a flame retardant and a colorant can be incorporated in the above-mentioned polypropylene composition, so far as the heat resistance, softness and mechanical strength of the film of the present invention are not degraded.

The obliquely oriented polypropylene cross film is generally prepared by laminating two polypropylene films so that the molecular orientation directions cross each other, but in the field where a high mechanical strength is required, at least three films can be laminated so that the molecular orientation directions cross one another.

The thickness of the laminated, obliquely oriented cross film is such that, for example, in case of a laminate of two obliquely oriented propylene films, the thickness of each starting oriented polypropylene film is 30 to 50 μ, the thickness of the adhesive later is 10 to 20 μ and the total thickness is about 100 μ.

A low-density polyethylene type adhesive resin is used as the adhesive layer (laminated resin) for a film of the above-mentioned composition composed of polypropylene and polyethylene, and a low-density polyethylene resin obtained by the high-pressure method, which has a density of 0.91 to 0.93 g/cm$^3$ and MFR of 5 to 20 g/10 min, is especially preferably used. Low-density polyethylene can be used singly, but in order to obtain a stronger bonding, it is preferred that an adhesive resin composed of a mixture obtained by blending low-density polyethylene with 10 to 40% by weight, especially 25 to 35% by weight, of an ethylene/α-olefin random copolymer, particularly a mixture obtained by blending high-pressure method low-density polyethylene having the above-mentioned density and MFR with 25 to 35% by weight of an ethylene/butene-1 random copolymer, be used.

As the α-olefin constituting the ethylene/α-olefin copolymer, there can be mentioned, for example, propylene, butene-1 and pentene-1.

The so-obtained obliquely oriented polypropylene film has an excellent heat resistance, as is understood from the description of the examples given hereinafter. Accordingly, it is possible to perform secondary processing by heating and to provide a product that can be widely used in various fields, and the cross film of the present invention is most preferably used as a fastening tape of a paper diaper which is now widespread.

The fastening tape is a fastener in the form of a sticking tape used as a fastening member of a paper diaper. For the fastening tape, it is required that in order to prevent breaking of the tape, the tensile strength and tear strength of the base should be high, and the base should resist a heating temperature (ordinarily, about 100° to about 180° C.) adopted for coating and drying a sticking agent. If the obliquely oriented polypropylene cross film obtained according to the present invention is used as the base, shrinkage or curling of the film is not caused when the sticking agent is coated and heated, and a fastening tape having a good dimension stability can be prepared.

As the sticking agent to be coated on the base, there can be used a polyolefin type sticking agent, an ethylene/vinyl acetate copolymer type sticking agent, an elastomer type sticking agent, a diene type sticking agent, an acrylic ester copolymer type sticking agent, a polyvinyl ether type sticking agent, a polyurethane type sticking agent and a polyamide type sticking agent. In view of the safety, coating stability, adhesion and stability with the lapse of time, a polyolefin type sticking agent, an ethylene/vinyl acetate copolymer type sticking agent and an elastomer type sticking agent are preferably used.

Coating of the sticking agent on the base is generally accomplished by a pan type roll coater, a nip feed type role coater, an extrusion coater, a slot coater or a gravure coater. The coating operation is generally carried out at a temperature of 120° to 180° C.

According to the present invention, by using a composition obtained by blending polypropylene as the main component with a specific amount of polyethylene, it becomes possible to form an obliquely oriented polypropylene film, and a cross film having excellent heat resistance, softness and mechanical strength can be obtained by laminating a plurality of so-obtained obliquely oriented films so that the molecular orientation directions cross one another. In this cross film, shrinkage or curling is not caused by secondary processing and the cross film has an excellent dimension stability, and therefore, the cross film can be preferably used as the base of a fastening tape for a paper diaper. Furthermore, the cross film can be effectively used as an adhesive tape and a base of a label.

The present invention will now be described in detail with reference to the following examples that by no means limit the scope of the invention.

The physical properties mentioned in the examples were determined according to the following methods.

(1) Thermal Shrinkage

The thermal shrinkage was determined by the MPC method. Namely, the thermal shrinkage was one determined after heating the sample in an oven at 140° C. for 5 minutes.

(2) Curling

The sample was heated at 140° C. for 5 minutes, and the appearance was examined and the curling state was evaluated according to the following rating.

○: good (no curl)

Δ: fair (slightly curled)

x: bad (conspicuously curled)

(3) Release Strength

The release strength was determined according to the method of JIS P-8139.

(4) Tear Strength

The tear strength was determined according to the method of JIS P-8116 (Elmendorf method).

(5) Impact Strength

The impact strength was determined according to the method of ASTM D-3420.

Incidentally, the shapeability was determined with respect to formation of a film having a thickness of 4.5 $\mu$ at a die temperature of 230° C. and an extrusion speed of 20 m/min.

The following properties were determined as the criterions indicating the softness.

(6) Tensile Characteristics

The tensile characteristics were determined according to the method of JIS K-6781.

(7) Stiffness

The stiffness was determined according to the method of JIS L-1096E.

The melt flow rate (MFR) is determined according to ASTM D-1238.

EXAMPLE 1 THROUGH 7 AND COMPARATIVE EXAMPLES 1 THROUGH 3

Films having a thickness of 45 u and an orientation angle of 45° were shaped from a composition comprising polypropylene having MFR of 0.5 (g/10 min) and a density of 0.910 (g/cm$^3$) and high-density polyethylene having MFR of 0.4 (g/10 min) and a density of 0.965 (g/cm$^3$) at a mixing ratio shown in Table 1.

Two of the obtained films were piled so that the orientation directions crossed each other at a crossing angle of 90°, and sandwich lamination was carried out according to customary procedures by using, as an intermediate adhesive layer, a blend comprising low-density polyethylene having MFR of 0.65 g/10 min and a density of 0.917 g/cm$^3$ and an ethylene/butene-1 copolymer having a crystallinity of 15% determined by the X-ray method, MFR of 3.6 g/10 min and a density of 0.88 g/cm$^3$, whereby an obliquely oriented cross film was obtained. The thickness of the adhesive layer was 10 $\mu$, and therefore, the entire thickness of the obtained obliquely oriented cross film was 100 $\mu$.

The thermal shrinkage, curling state, shapeability, tensile characteristics and stiffness of the obtained obliquely oriented cross film were evaluated. The obtained results are shown in Table 1.

TABLE 1

| | Composition of Film (polypropylene/polyethylene) | Thermal Shrinkage MD | Thermal Shrinkage TD | Curling (organoleptic evaluation) | Shapeability (starting film) | Tensile Characteristics, Apparent Young's Modulus (kg/cm$^2$) (MD/TD) | Stiffness (kg/cm$^2$) (MD/TD) |
|---|---|---|---|---|---|---|---|
| Comparative Example 1 | 100/0 | 0.6 | 0.1 | ○ | Shaping impossible (because of insufficient melt tension, melt was caught on mandrel, and occurrence of puncture and shaking was conspicuous) | 11,500/12,000 | 120/130 |
| Example 1 | 85/15 | 1.0 | 1.4 | ○ | good | 10,000/9,500 | 100/105 |
| Example 2 | 70/30 | 1.2 | 1.6 | ○ | good | 9,500/9,000 | 75/80 |
| Example 3 | 50/50 | 2.6 | 2.4 | ○ | good | 9,000/8,500 | 70/75 |
| Comparative Example 2 | 35/65 | 5.0 | 3.5 | Δ | good | 8,500/8,000 | 65/70 |
| Comparative Example 3 | 0/100 | molten | | X | good | 7,500/7,000 | 60/65 |

In order to examine the influences of the mixing ratio of the components in the adhesive layer (laminated resin) in the obliquely oriented cross film shaped from the composition comprising 70 parts by weight of polypropylene and 30 parts by weight of high-density polyethylene, the release strength, tear strength, impact strength, tensile characteristics and stiffness were measured while changing the blending ratio between the low-density polyethylene (PE) and the ethylene/butene-1 copolymer (E-αO). The obtained results are shown in Table 2.

TABLE 2

| Example No. | Laminated Resin Pe/E-αO | Release Strength g/15 mm width | Tear Strength MD | Tear Strength TD | Impact Strength (directly read value, kg.cm) | Tensile Characteristics, Apparent Young's Modulus (kg/cm$^2$) (MD/TD) | Stiffness (kg/cm$^2$) (MD/TD) |
|---|---|---|---|---|---|---|---|
| 4 | 100/0 | 10 | 10 | 20 | 14.0 | 9,500/9,000 | 75/80 |
| 5 | 93/7 | 13 | 14 | 30 | 14.5 | 9,500/9,000 | 75/80 |
| 6 | 85/15 | 25 | 20 | 60 | 16.0 | 9,500/8,500 | 70/75 |
| 7 | 70/30 | 150 | 75 | 150 | 18.0 | 8,500/8,000 | 65/70 |

EXAMPLE 8

Referring to FIG. 1 illustrating a typical instance of the fastening tape for a paper diaper according to the present invention, polypropylene films 1A and 1B having a molecular orientation in a certain oblique direction were bonded and laminated through an adhesive 2 composed of a mixture of low-density polyethylene and an ethylene/α-olefin copolymer, and a sticking agent 3 was coated on the surface confronting an intertape (not shown), that is, the surface of the film 1B.

Figure 3:
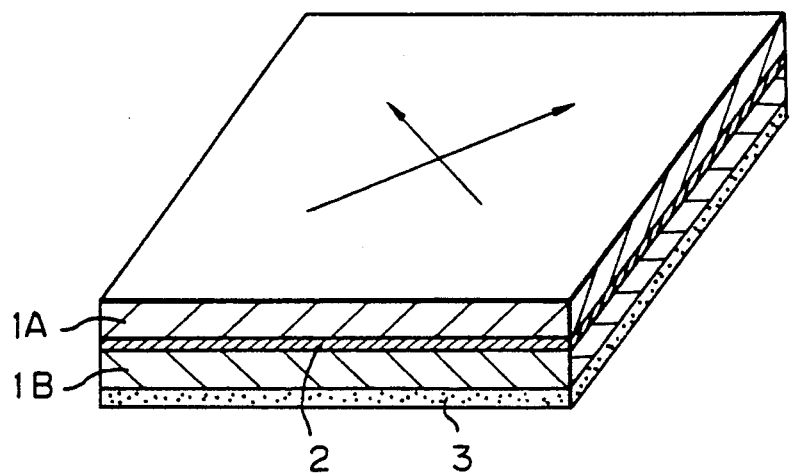
FIG. 3 is perspective view of the fastening tape.

As is seen from FIG. 3, which is a perspective view of the fastening tape, the polypropylene films 1A and 1B were bonded and laminated through the adhesive 2 so that the orientation directions crossed each other, whereby an obliquely oriented cross film was constructed.

Figure 2:
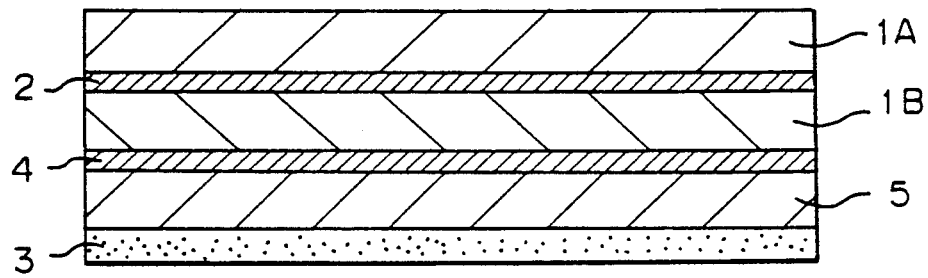

Referring to FIG. 2, which is a sectional view showing another instance of the fastening tape for a paper diaper according to the present invention, a nylon film or polyester film 5 was dry-laminated on the lower surface of the above-mentioned cross film, and a sticking agent 3 was coated on the lower surface of the film 5.

If the surface of the polypropylene film 1A, constituting the surface layer of the fastening tape, was subjected to a corona surface treatment, the surface of the fastening tape could be freely printed, and therefore, a colorful fastening tape having a decorative effect could be provided.

From the data of the apparent Young's modulus and stiffness shown in Tables 1 and 2, the following can be seen.

(1) The smaller is the amount of PP shown in Table 1, the better is the softness of the film.

(2) The larger is the amount of E-αO in the laminated resin shown in Table 2, the better is the softness of the tape.

(3) The softness is improved by the presence of the laminates resin of the intermediate layer in the three-layer structure, and a good soft touch is given by dint of the laminated resin as well as the features (1) and (2) mentioned above.

We claim:

1. An obliquely oriented polypropylene cross film, which comprises a laminate of a plurality of polypropylene films having a molecular orientation in an oblique direction, which are laminated so that the molecular orientation directions cross one another, said polypropylene films being shaped from a composition comprising 50 to 90 parts by weight polypropylene having an MFR of 0.5 to 10 g/10 min and 10 to 50 parts by weight of polyethylene having a density of 0.940 to 0.950 and an MFR of 0.01 to 10 g/10 min, said polypropylene films being laminated such that the molecular orientation directions of the respective films cross one another with a crossing angle between the orientation directions falling within the range of 30° to 150° in the length direction of the film.

2. An obliquely oriented polypropylene cross film as set forth in claim 1 wherein adjacent polypropylene films are laminated to each other with a layer of adhesive composed of a mixture comprising low-density polyethylene obtained by the high-pressure method, which has a density of 0.91 to 0.93 g/cm$^3$ and MFR of 5 to 20 g/10 min and an ethylene/α-olefin copolymer.

3. An obliquely oriented polypropylene cross film as set forth in claim 2, wherein the ethylene/α-olefin copolymer is an ethylene/butene-1 random copolymer.

4. The obliquely oriented polypropylene cross film of claim 2 comprising two obliquely oriented polypropylene films, wherein the thickness of each film is 30 to 50 μ, the thickness of the adhesive layer is 10 to 20 μ and the total thickness is about 100 μ.

5. The obliquely oriented polyproplene cross film of claim 1, wherein the bonding strength between the obliquely oriented film is from 100 to 400 g/15 mm.

6. A fastening tape for a paper diaper, which comprises (i) a laminate of a plurality of polypropylene films having a molecular orientation in an oblique direction, and (ii) a layer of a sticking agent coated on a surface of the laminate, said polypropylene films being shaped from a composition comprising 50 to 90 parts by weight of polypropylene having a melt flow rate (MFR) of 0.5 to 10 g/10 min and 10 to 50 parts by weight of polyethylene having a density of 0.940 to 0.965 g/cm$^3$ and a melt flow rate (MFR) of 0.01 to 10 g/10 min, and said polypropylene films being laminated so that the molecular orientation directions of the respective films cross one another and that the crossing angle between the two orientation directions is within the range of 30° to 150° in the length direction of the films.

* * * * *